United States Patent [19]
Van Sickle

[11] Patent Number: 5,994,564
[45] Date of Patent: Nov. 30, 1999

[54] MONOESTERS AND MACROCYCLIC DIESTER OF PHTHALIC ACID AND SYNTHESIS THEREOF

[75] Inventor: Dale E. Van Sickle, Kingsport, Tenn.

[73] Assignee: Eastman Chemical Company, Kingsport, Tenn.

[21] Appl. No.: 09/136,452

[22] Filed: Aug. 19, 1998

Related U.S. Application Data

[60] Provisional application No. 60/058,878, Sep. 15, 1997.

[51] Int. Cl.$^6$ .................................................. C07D 321/00
[52] U.S. Cl. ............................................................ 549/267
[58] Field of Search .............................................. 549/267

[56] References Cited

FOREIGN PATENT DOCUMENTS 0 234 902 A2   9/1997   European Pat. Off. .

OTHER PUBLICATIONS

Carothers, W.H., *Collected Papers of Wallace Hume Carothers on High Polymeric Substances,* Eds. H. Mark and G.S. Whitby, Interscience Publishers, Inc., 248–259 (1940).
Bradshaw et al., *Chem. Revs.* 79:37 (1979).
Ehrhart, W. A., *J. Org. Chem.* 33:2930 (1968).
Drewes et al.,*J.C.S. Perkin I,* 2148 (1972).
Chen et al.,*J. Applied Appl. Polym Sci.* 41:2517 (1990).
Löfgren et al.,*J.M.S. Rev. Mocaromo. Chem. Phys.,* C35(3), 379–418 (1995).
Chemical Abstracts No. 293666, "Synthesis, Structure and Ring–opening Polymerization of Macrocyclic Arylates Containing Phthalic Unit," vol. 127, No. 21 (1997).
Database WPI 97–115341, Week 8711, "Preparation of Biodegradable Polymer Cpd.. For Bag Or Sheet—by Ring–opening, Co–polymerization of Cyclic Acid Anhydride and Cyclic Ether with Magnesium Chloride," (1997).

*Primary Examiner*—Ba K. Thrinh

[57] ABSTRACT

Monoesters and macrocyclic diesters of 2,2,4-trimethyl-1,3-pentanediol and phthalic acid or a derivative thereof are described. Methods by which such monoesters and diesters may be prepared are also described. The mono- and diesters according to the invention are useful in the preparation of clear, hard thermoplastic polymers. The thermoplastic polymers are useful in coatings, inks, reinforced plastics and packaging materials.

13 Claims, No Drawings

MONOESTERS AND MACROCYCLIC DIESTER OF PHTHALIC ACID AND SYNTHESIS THEREOF

This application claims priority of provisional application(s) No. 60/058,878 filed on Sep. 15, 1997 which is incorporated herein by reference.

BACKGROUND OF THE INVENTION

1. Field of the Invention

The invention relates to monoesters and a macrocyclic diester of phthalic acid and derivatives thereof. Such esters of phthalic acid and derivatives thereof are useful in the preparation of thermoplastic polymers. The thermoplastic polymers may be used to prepare coatings, inks, reinforced plastics and packaging.

2. Description of the Related Art

The synthesis of lactones, or cyclic esters, derived from either hydroxyacids or from diacids and dihydroxy compounds is well known to the art. (Carothers, W. H., *Collected Papers of Wallace Hume Carothers on High Polymeric Substances*, Eds. H. Mark and G. S. Whitby, Interscience Publishers, Inc., 248–259 (1940)). Examples include δ-valerolactone, prepared by cyclization of 5-hydroxypentanoic acid, and lactide, prepared by the dimerization of lactic acid. These simple compounds which contain six-membered lactone rings are readily prepared in good yield, as are similar lactones with five atoms in the ring, such as γ-butyrolactone. Seven-membered ring lactones, such as, for example, ε-caprolactone, can also be readily prepared. However, the synthesis of lactones with larger rings, particularly those with eight to twelve ring atoms, has proven to be more difficult.

Macrocyclic di- and tetraester compounds, including cyclic esters derived from equimolar amounts of o-phthalic acid and a glycol, have been prepared. (Bradshaw et al., *Chem. Revs.* 79:37 (1979)). However, the diesters, in particular those forming eight- to ten-membered rings, prepared from o-phthalic acid and simple glycols such as 1,2-dihydroxyethane, 1,3-dihydroxypropane, and 2-methyl-1,3-dihydroxypropane, were recovered in poor yields of less than 5%. (Ehrhart, W. A., *J. Org. Chem.* 33:2930 (1968)). The poor yields are believed to be due to inherent ring strain as a result of the two carbonyl groups. (Drewes et al., *J. C. S. Perkin I*, 2148 (1972)). The synthesis of a cyclic tetraester compound from phthalic anhydride and 1,3-dihydroxy-2,2-dimethylpropane was also achieved in very low yields of only 1.7%. (Chen et al., *J. Applied Appl. Polym Sci.* 41:2517 (1990)).

There still exists a need in the art for a synthetic route to prepare cyclic esters or lactones from a phthalic acid derivative and a simple glycol in high yield and purity. The cyclic esters provide unique intermediates in the production of thermoplastic polymers such as polyesters. These polyesters can be used in coatings, inks, reinforced plastics and packaging.

SUMMARY OF THE INVENTION

The invention relates a macrocyclic diester of formula (III):

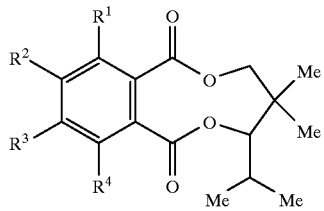

The invention also relates methods of preparing a diester of formula (III) by contacting, optionally in the presence of a catalyst, a phthalic acid derivative of formula (I):

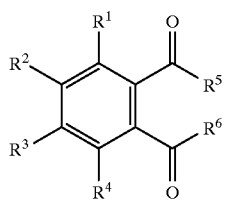

with the glycol 2,2,4-trimethyl-1,3-pentane diol (TMPD):

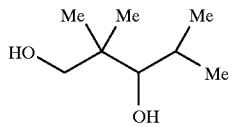

The invention also relates a thermoplastic polymer resulting from the ring opening polymerization of a diester of formula (III).

The invention still further relates a monoester of formula (II):

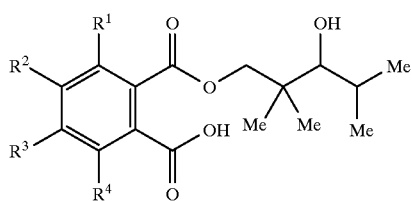

A monoester of formula (II) is an intermediate which can be isolated in the reaction of a phthalic acid derivative of formula (I) with TMPD to form a macrocyclic diester of formula (III).

DETAILED DESCRIPTION OF THE DRAWING

One embodiment of the invention is a macrocyclic diester of formula (III):

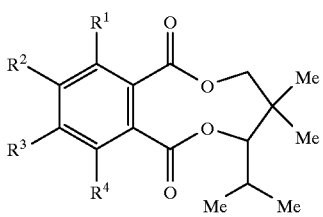

(III)

In formula (III), $R^1$, $R^2$, $R^3$ and $R^4$ are, independently, hydrogen, a substituted or unsubstituted $C_1$–$C_{10}$ alkyl, aryl, or heteroaryl group, a nitro group, a halo group (F, Cl, Br, and I), a thio group, or an amino group. A combination of any two adjacent substituents, $R^1$, $R^2$, $R^3$ and $R^4$, together with the phenyl ring may also form a fused aromatic ring structure such as anthracene or naphthalene. Preferably, $R^1$, $R^2$, $R^3$ and $R^4$ are each a hydrogen. Alternatively, at least one of $R^1$, $R^2$, $R^3$ and $R^4$ is a $C_1$–$C_4$ alkyl group.

The invention also includes a method of preparing a macrocyclic diester of formula (III) via an esterification reaction. In a method of the invention, a macrocyclic diester of formula (III) may be prepared by contacting under suitable reaction conditions, for example in a suitable solvent and, optionally, in the presence of a catalyst, a phthalic acid derivative of formula (I):

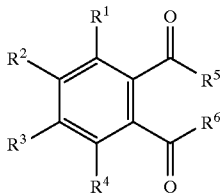

(I)

with 2,2,4-trimethyl-1,3-pentane diol (TMPD):

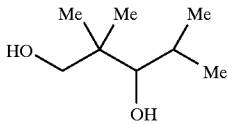

In formula (I), $R^1$, $R^2$, $R^3$ and $R^4$ are as defined above while $R^5$ and $R^6$ are independently a hydroxyl group, a chloride group or, when taken together, an oxygen to form a phthalic acid anhydride or its derivative. The reaction may be carried out using typical esterification reaction conditions known in the art. Preferably, such a method is conducted under azeotropic distillation conditions known in the art. Azeotropic distillation conditions remove water from the reaction and moves the reaction toward completion, i.e. the formation of a macrocyclic diester of formula (III).

To prepare a macrocyclic diester of formula (III), the molar ratio of a phthalic acid derivative of formula (I) to TMPD is preferably about 1:1. A slight molar excess of TMPD may be used without effecting the yield of a diester of formula (III). A large molar excess of generally greater than about 50% of either reactant should be avoided since such conditions renders purification of the desired macrocyclic diester of formula (III) difficult by increasing the production of potential by-products. Such by-products may include a monoester resulting from the reaction between the phthalic acid derivative and the secondary alcohol position of 2,2,4-trimethyl-1,3-pentane diol (TMPD) and diester isomers. By using a large molar excess of either reactant, the overall yield of the desired macrocyclic diester may be significantly reduced.

The phthalic acid derivative may be any phthalic acid derivative of formula (I) as described above capable of forming ester linkage(s) upon reaction with TMPD. Preferably the phthalic acid derivative is phthalic anhydride, phthalic acid or phthaloyl chloride.

The esterification reaction is preferably accomplished using a catalyst. The catalyst may be any esterification catalyst known in the art. The catalyst preferably increases the rate of the reaction and the yield of desired product. Examples of suitable catalysts, include, but are not limited to, sulfonic acids, stannoic acid, titanium salts, manganese salts, and the like. Preferably the catalyst is butyl stannoic acid [(BuSn(O)OH]. Butyl stannoic acid is sold as FASCAT® 4100 available from Elf Atochem of Philadelphia, Pa. Preferably, about 0.001 to 0.01 moles catalyst per mole of phthalic acid derivative of formula (I) is used.

Suitable solvents for the esterification reaction are those which dissolve the reactants or facilitate esterification. Preferably, the solvent facilitates the removal of water as an azeotrope, i.e. azeotropic distillation as discussed above. Examples of suitable solvents include, but are not limited to, benzene, toluene and xylene. Preferably, the solvent is toluene or xylene. The amount of solvent used allows for combined reactant concentrations of between 10%–40% by weight of the reaction system. Excess solvent increases costs of production due to the added cost of the excess solvent, cost of recovery and/or disposal of the excess solvent, and cost of extra equipment required to run the reaction. Too little solvent produces high reactant concentrations which may promote oligomer formation at the expense of diester formation.

The esterification reaction may be conducted at temperatures ranging from about 50°–150° C. More preferably, the reaction temperature ranges from about 100°–135° C. Oligomer formation may also be promoted by excessively high reaction temperatures, especially in combination with high reactant concentrations.

In a method of the invention, the esterification reaction of a phthalic acid derivative of formula (I) with 2,2,4-trimethyl-1,3-pentane diol (TMPD) may be conducted to first form a monoester of formula (II):

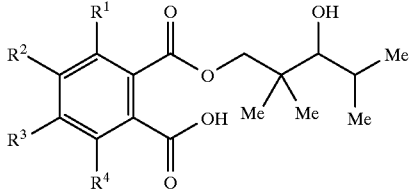

(II)

In formula (II), $R^1$, $R^2$, $R^3$ and $R^4$ are as defined above. If desired, the monoester of formula (II) may be isolated and purified by techniques known in the art such as, for example, recrystallization from toluene. A macrocyclic diester of formula (III) may be prepared by heating an isolated monoester of formula (II) under suitable reaction conditions, for example in a suitable solvent and, optionally, in the presence of a catalyst. Preferably, the conversion of an isolated monoester of formula (II) to a macrocyclic diester of formula (III) is conducted under azeotropic distillation conditions as described above.

To promote the production of a monoester of formula (II) without conversion of the monoester to a macrocyclic diester of formula (III), the reaction may be conducted at temperatures ranging between 50–90° C. Preferably, monoester production is conducted at temperatures ranging between 75–85° C. Conducting this reaction within the above temperature range favors production of the monoester without conversion to the diester.

Completion of the esterification reactions discussed above may be determined by monitoring reactant consumption and macrocyclic diester or monoester formation. Consumption of the reactants and production of the macrocyclic diester may be monitored by techniques known in the art. These techniques include, for example, chromatography with vapor phase chromatography (vpc) being a preferred technique. When using vpc, to obtain a better analysis, the sample may first be derivatized, for example, with trimethylsilyl groups using bis(trimethylsilyl)trifluoroacetamide (BSTFA, commercially available from Aldrich Chemical Company of Milwaukee, Wis.).

When the esterification reaction is complete, the reaction solvent may be removed to yield a solid containing the desired product, e.g., the macrocyclic diester of formula (III) or the monoester of formula (II). The reaction solvent may be removed using techniques known in the art, such as distillation, particularly distillation under reduced pressure, for example using a rotary evaporator.

The product macrocyclic diester of formula (III) or diester of formula (II) may then be purified using known techniques such as recrystallization from an appropriate solvent. A macrocyclic diester of formula (III) may be recrystallized from solvents such as ethanol, methanol and the like. A monoester of formula (II) may be recrystallized from solvents such as toluene, xylene and the like. Preferably, a macrocyclic diester of formula (III) may be recrystallized from methanol, and a monoester of formula (II) may be recrystallized from toluene. As is known on the art, the purified product may then be washed, for example with a small amount of the recrystallization solvent, to remove residual impurities.

Using reaction conditions discussed above, a macrocyclic diester of formula (III) may be obtained in yields of about 40% or greater. After purification, using techniques known in the art as described above, the macrocyclic diester of formula (III) of >99% purity may be isolated by techniques known in the art such as vacuum filtration.

Another embodiment of the invention is a thermoplastic polymer formed from a diester of formula (III). A thermoplastic polymer of a diester of formula (III) may be prepared by a ring opening polymerization of a diester of formula (III) in the presence of a catalyst and heat. Ring opening polymerizations of cyclic diesters to form polyesters are known in the art and may be used to form the thermoplastic polymer of the invention. (Löfgren et al., *J. M. S. Rev. Mocaromo. Chem. Phys.*, C35(3), 379–418 (1995)). The catalyst may be any ring opening polymerization catalyst known in the art, with dibutyl tin oxide being a preferred catalyst. The ring opening polymerization reaction may be conducted at temperature ranging between 150°–250° C., preferably, between 160°–180° C. Excessively high temperatures of >250° C. should be avoided since polymer darkening and degradation may result. The ring opening polymerization process is also preferably conducted in an inert atmosphere and at pressures ranging from reduced pressure to slightly superatmospheric pressure. Preferably, the combination of temperature and pressure is such that little to none of diester of formula (III) volatilizes and escapes from the system.

The thermoplastic polymer according to the invention exhibits exceptional resistance to weathering and hydrolysis due to the highly substituted nature of TMPD. In addition, the thermoplastic polymer according to the invention exhibits high molecular weight and low polydispersity. A polyester of the invention may be used as the resin base in coatings, inks, reinforced plastics and packaging materials.

The following examples are given to illustrate the present invention. It should be understood, however, that the invention is not to be limited to the specific conditions or details described in these examples.

EXAMPLE 1

Synthesis of 7-Isopropyl-8,8-dimethyl-8,9-dihydro-7H-6,10-dioxabenzocyclononene-5,11-dione in the Presence of a Catalyst A solution of 14.8 g (0.10 mol) of phthalic anhydride, 16.1 g (0.11 mol) of 2,2,4-trimethyl-1,3-pentanediol (TMPD), and 0.036 g of butyl stannoic acid, [(BuSn(O)OH], (FASCAT® 4100 catalyst) in 125 mL of toluene was refluxed under a short packed column fitted with a Dean-Stark trap for removal of water as it formed, until analysis by vapor phase chromatography (vpc) indicated that reaction was complete. Distillation of the residue (30.0 g) at ~0.9 torr, with gentle heating of the still pot by means of a 1200 watt heat gun, gave 11.3 g (40% yield) of product which distilled at a vapor temperature between 140° and 155° C. The distillate formed a hard cake on standing which was recrystallized from methanol (recoveries, 62–67%) to give pure 7-Isopropyl-8,8-dimethyl-8,9-dihydro-7H-6,10-dioxabenzocyclononene-5,11-dione, m.p. (differential scanning calorimetry) 101.24° C.

Analysis: Mol. wt. calcd. for $C_{16}H_{20}O_4$: 276. Found: (FDMS; $M^{+1}$), 277. $^1$H NMR ($CDCl_3$), δ7.86 (1H); 7.74–7.58 (m, 3H); 4.09 (d, 1H); 3.96 (d, 1H); 3.49 (d, 1H); 1.93 (m, 1H); 1.30 (s, 3H); 1.00 (d, 3H); 0.92 (s, 3H); 0.90 (d, 3H).

EXAMPLE 2

Synthesis of 7-Isopropyl-8,8-dimethyl-8,9-dihydro-7H-6,10-dioxabenzocyclononene-5,11-dione in the Presence of a Catalyst A mixture of 74.0 g (0.50 mol) of phthalic anhydride, 80.5 g (0.55 mol) of 2,2,4-trimethyl-1,3-pentanediol (TMPD), and 600 mL of toluene was stirred and warmed. When the solid had dissolved, 0.2 g of butyl stannoic acid (FASCAT® 4100 catalyst) was added and the resulting mixture was heated to reflux. After approx. 90 hr, analysis of the mixture by vapor phase chromatography (vpc) indicated that, on a toluene-free basis, it contained 74.23% of 7-Isopropyl-8,8-dimethyl-8,9-dihydro-7H-6,10-dioxabenzocyclononene-5,11-dione, 4.05% of TMPD, 1.84% of phthalic anhydride, 0.63% and 1.78%, respectively of each of the two isomeric monoesters of phthalic acid and TMPD, and 1.12%, 6.76%, and 9.22%, respectively, of each of the three diesters of phthalic acid and TMPD. No phthalic acid was present.

Toluene was removed from the mixture on a rotary evaporator (20 torr., 70° C.). The residue (151.9 g) was a thick syrup which crystallized slowly on standing. This residue was stirred with 150 mL of methanol, the mixture chilled to 0° C. overnight, then filtered at –10° C. The solid was washed with a small amount of chilled methanol and dried to give 73.7 g (75% pure by vpc; 40% yield) of crude 7-Isopropyl-8,8-dimethyl-8,9-dihydro-7H-6,10- dioxabenzocyclononene-5,11-dione. Recrystallization of 50.0 g of crude 7-Isopropyl-8,8-dimethyl-8,9-dihydro-7H-6,10-dioxabenzocyclononene-5,11-dione from 100 mL of methanol with cooling to approx. 0° C. gave 42.5 g (85% recovery) of pure 7-Isopropyl-8,8-dimethyl-8,9-dihydro-7H-6,10-dioxabenzocyclononene-5,11-dione as a white crystalline solid.

Analysis: (vapor phase chromatography; diphenyl internal standard): 7-Isopropyl-8,8-dimethyl-8,9-dihydro-7H-6,10-dioxabenzocyclononene-5,11-dione, 99.97%.

EXAMPLE 3

Synthesis of 7-Isopropyl-8,8-dimethyl-8,9-dihydro-7H-6,10-dioxabenzocyclononene-5,11-dione in a More Concentrated Solution Following the procedure of Examples 1 or 2, 7-Isopropyl-8,8-dimethyl-8,9-dihydro-7H-6,10-dioxabenzocyclononene-5,11-dione was prepared from a solution of 14.81 g (0.1 mole) of phthalic anhydride and 16.30 g (0.11 mole) of 2,2,4-trimethyl-1,3-pentanediol (TMPD) in 75 mL of xylene. The catalyst was 49.4 mg of FASCAT® 4100 catalyst. Xylene was removed on a rotary evaporator and the residue distilled to give 11.09 g of distillate, $b_{0.5}$ 130–160° C. which was found by vapor phase chromatography (vpc) to consist of 84% of 7-Isopropyl-8,8-dimethyl-8,9-dihydro-7H-6,10-dioxabenzocyclononene-5,11-dione (40% yield). The residue from this distillation weighed 17.65 g.

EXAMPLE 4

Synthesis of 7-Isopropyl-8,8-dimethyl-8,9-dihydro-7H-6,10-dioxabenzocyclononene-5,11-dione in a More Dilute Solution, Without the Addition of a Catalyst.

A solution of 114.82 g (0.10 mole) of phthalic anhydride and 16.31 g (0.11 mole) of 2,2,4-trimethyl-1,3-pentanediol (TMPD) in 250 mL of xylene was heated for 96 hr as described in Examples 1–3. Xylene was removed on a rotary evaporator at 20 torr, at a base temperature of 68° C. The residue (30.0 g) was diluted with 30 mL of methanol and the resulting slurry cooled to 1° C., filtered, and washed with methanol which had been chilled to −20° C. to give 15.9 g (58% yield) of 7-Isopropyl-8,8-dimethyl-8,9-dihydro-7H-6,10-dioxabenzocyclononene-5,11-dione, which was 99.9% pure by vapor phase chromatography (vpc). The methanol washing from recovery of 7-Isopropyl-8,8-dimethyl-8,9-dihydro-7H-6,10-dioxabenzocyclononene-5,11-dione contained, on a methanol-free basis, 16.4% of 7-Isopropyl-8,8-dimethyl-8,9-dihydro-7H-6,10-dioxabenzocyclononene-5,11-dione, while the residue from stripping xylene from the original reaction mixture contained 41.2% of 7-Isopropyl-8,8-dimethyl-8,9-dihydro-7H-6,10-dioxabenzocyclononene-5,11-dione.

EXAMPLE 5

Synthesis of 7-Isopropyl-8,8-dimethyl-8,9-dihydro-7H-6,10-dioxabenzocyclononene-5,11-dione in the Presence of a 100% Molar Excess of 2,2,4-trimethyl-1,3-pentanediol (TMPD)

The procedure of the preceding examples was followed, with a solution of 14.81 g (0.1 mole) of phthalic anhydride and 29.27 g (0.20 mole) of 2,2,4-trimethyl-1,3-pentanediol (TMPD) in 250 mL of xylene. Analysis of the residue, after removal of the xylene solvent indicated that it contained 41.3% of 7-Isopropyl-8,8-dimethyl-8,9-dihydro-7H-6,10-dioxabenzocyclononene-5,11-dione, 30.9% of diesters of phthalic acid and TMPD, and 24.0% of TMPD. The residue (28.17 g) was distilled at 2–3 torr and a pot temperature of 200–220° C. to give a distillate (12.60 g) which contained by vapor phase chromatography (vpc) 78.9% of TMPD and 15.5% of 7-Isopropyl-8,8-dimethyl-8,9-dihydro-7H-6,10-dioxabenzocyclononene-5,11-dione. The residue was diluted with cold methanol, filtered, and the crystals washed with cold methanol to give 13.21 g (99.0% pure by vpc; 48% yield) of 7-Isopropyl-8,8-dimethyl-8,9-dihydro-7H-6,10-dioxabenzocyclononene-5,11-dione. The residue and washings from this separation of 7-Isopropyl-8,8-dimethyl-8,9-dihydro-7H-6,10-dioxabenzocyclononene-5,11-dione contained, on a methanol-free basis, 13.1% of 7-Isopropyl-8,8-dimethyl-8,9-dihydro-7H-6,10-dioxabenzocyclononene-5,11-dione and 52.6% of diesters of phthalic acid and TMPD.

EXAMPLE 6

Preparation of a Linear Polymer by Ring Opening of 7-Isopropyl-8,8-dimethyl-8,9-dihydro-7H-6,10-dioxabenzocyclononene-5,11-dione A mixture of 1.994 g of recrystallized 7-Isopropyl-8,8-dimethyl-8,9-dihydro-7H-6,10-dioxabenzocyclononene-5,11-dione and 8.0 mg of dibutyltin oxide was placed in a tube, degassed with the cyclic diester just above the melting point (101° C.) and sealed under vacuum. The tube was heated in an oil bath at 170° C. for approx. 96 hr. The resulting viscous, yellow product solidified to a hard glass at room temperature. Gel phase chromatography indicated that the product contained phthalic anhydride and some residual monomer but that the polymeric portion had number average molecular weight (Mn)=6700; weight average molecular weight (Mw)=9600. The glass transition temperature (differential scanning calorimetry; second heat) was 39.0° C.

EXAMPLE 7

Preparation of 1-(2,2,4-Trimethyl-1,3-pentanediol) monophthalate

A solution of 4.98 g (0.033 mole) of phthalic anhydride and 5.42 g (0.037 mole) of TMPD in 40 mL of toluene was stirred and heated at 80° C. for approximately 30 hr. The solvent was evaporated and the crystalline residue washed with cold toluene and dried to give 5.95 g of 2,2,4-Trimethyl-1,3-pentanediol monophthalate. Crude 2,2,4-Trimethyl-1,3-pentanediol monophthalate (1.00 g) was recrystallized from 5 mL of toluene and washed to give 0.95 g of pure 1-(2,2,4-Trimethyl-1,3-pentanediol) monophthalate, m. p. (differential scanning calorimetry) 127.0° C.

Analysis: Calcd for $C_{16}H_{22}O_5$: Mol. wt., 294.1467. Found (mass spectrometry): 294.1461.

EXAMPLE 8

Conversion of 1-(2,2,4-Trimethyl-1,3-pentanediol) monophthalate to 7-Isopropyl-8,8-dimethyl-8,9-dihydro-7H-6,10-dioxabenzocyclononene-5,11-dione A solution of 29.4 g (0.100 mol) of 2,2,4-Trimethyl-1,3-pentanediol monophthalate in 250 mL of toluene was allowed to stand over a weekend, 32.6 mg of catalyst FASCAT 4100® was added, and the solution was allowed to reflux under a Dean-Stark trap for 102 hr, when 1.40 mL of water had collected in the trap. Toluene was removed on the rotary evaporator. Analysis of this residue by vapor phase chromatography (vpc) indicated that it contained 72% of 7-Isopropyl-8,8-dimethyl-8,9-dihydro-7H-6,10-dioxabenzocyclononene-5,11-dione, as well as minor amounts of 2,2,4-trimethyl-1,3-pentanediol (TMPD), phthalic anhydride, 1-(2,2,4-Trimethyl-1,3-pentanediol) monophthalate, 3-(2,2,4-Trimethyl-1,3-pentanediol) monophthalate, and diesters of phthalic acid and TMPD. This residual oil (28.9 g.) was diluted with 30 mL of methanol, seeded with a small crystal of the pure 7-Isopropyl-8,8-dimethyl-8,9-dihydro-7H-6,10-dioxabenzocyclononene-5,11-dione and cooled to 0° C., and filtered. The crystals were washed with methanol. The purified solid weighed 15.33 g. Analysis by vpc indicated that it was 99% pure 7-Isopropyl-8,8-dimethyl-8,9-dihydro-7H-6,10-dioxabenzocyclononene-5,11-dione (55% yield).

The filtrate from the methanol recrystallization was evaporated to remove the solvent. The residual oil (13.3 g.) was analyzed by vpc. It contained 24.1% of 7-Isopropyl-8,8-dimethyl-8,9-dihydro-7H-6,10-dioxabenzocyclononene-5,11-dione, together with lesser amounts of the components noted in the residual oil from the original toluene evaporation.

The claimed invention is:

1. A macrocyclic diester of formula (III):

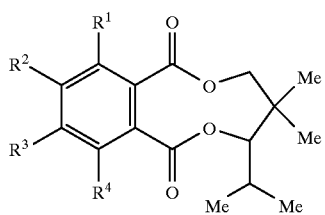
(III)

where $R^1$, $R^2$, $R^3$, and $R^4$ are, independently, hydrogen, a substituted or unsubstituted $C_1$–$C_{10}$ alkyl, aryl, or heteroaryl group, a nitro group, a halo group, a thio group, or an amino group; and any two adjacent substituents of $R^1$, $R^2$, $R^3$, and $R^4$ when taken together with the phenyl ring forms a fused aromatic ring structure.

2. A macrocyclic diester of claim 1, wherein $R^1$, $R^2$, $R^3$, and $R^4$ are independently a hydrogen, or a $C_1$–$C_4$ alkyl group; or any two adjacent substituents, $R^1$, $R^2$, $R^3$ and $R^4$, together with the phenyl ring form a fused aromatic ring structure selected from anthracene and naphthalene.

3. A macrocyclic diester of claim 1, wherein $R^1$, $R^2$, $R^3$, and $R^4$ are each a hydrogen.

4. A method of preparing a macrocyclic diester comprising the step of:

contacting, optionally in the presence of a catalyst, 2,2,4-trimethyl-1,3-pentanediol and a phthalic acid derivative of formula (I):

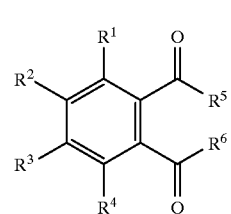
(I)

where $R^1$, $R^2$, $R^3$, and $R^4$ are, independently, hydrogen, a substituted or unsubstituted $C_1$–$C_{10}$ alkyl, aryl, or heteroaryl group, a nitro group, a halo group, a thio group, or an amino group;

any two adjacent substituents of $R^1$, $R^2$, $R^3$, and $R^4$ when taken together with the phenyl ring forms a fused aromatic ring structure; and $R^5$ and $R^6$ are independently a hydroxyl group, a chloride group or when taken together an oxygen;

under conditions sufficient to produce a diester of formula (III):

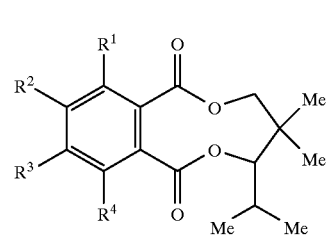
(III)

where $R^1$, $R^2$, $R^3$, and $R^4$ are, independently, hydrogen, a substituted or unsubstituted $C_1$–$C_{10}$ alkyl, aryl, or heteroaryl group, a nitro group, a halo group, a thio group, or an amino group; and any two adjacent substituents of $R^1$, $R^2$, $R^3$, and $R^4$ when taken together with the phenyl ring form a fused aromatic ring structure.

5. A method of claim 4, wherein said phthalic acid derivative is selected from the group consisting of phthalic anhydride, phthalic acid and phthaloyl chloride.

6. A method of claim 4, wherein $R^1$, $R^2$, $R^3$, and $R^4$ are each a hydrogen.

7. A method of claim 4, wherein said catalyst is butyl stannoic acid.

8. A method of claim 4, wherein said contacting step is performed under azeotropic distillation conditions.

9. A method of claim 4, wherein said contacting step of 2,2,4-trimethyl-1,3-pentanediol and a phthalic acid derivative of formula (I) first forms a monoester of formula (II) prior to said diester:

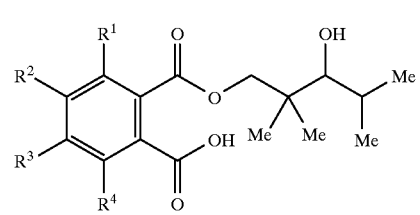
(II)

where $R^1$, $R^2$, $R^3$, and $R^4$ are, independently, hydrogen, a substituted or unsubstituted $C_1$–$C_{10}$ alkyl, aryl, or heteroaryl group, a nitro group, a halo group, a thio group, or an amino group; and any two adjacent substituents of $R^1$, $R^2$, $R^3$, and $R^4$ when taken together with the phenyl ring forms a fused aromatic ring structure.

10. A method of preparing a macrocyclic diester comprising the step of:

heating, optionally in the presence of a catalyst, a monoester of formula (II):

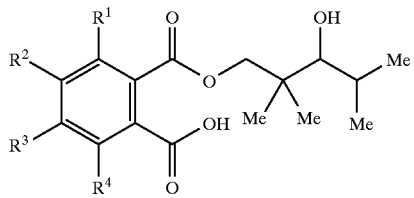

(II)

where $R^1$, $R^2$, $R^3$, and $R^4$ are, independently, hydrogen, a substituted or unsubstituted $C_1$–$C_{10}$ alkyl, aryl, or heteroaryl group, a nitro group, a halo group, a thio group, or an amino group; and any two adjacent substituents of $R^1$, $R^2$, $R^3$, and $R^4$ when taken together with the phenyl ring forms a fused aromatic ring structure; under conditions sufficient to produce a macrocyclic diester of formula (III):

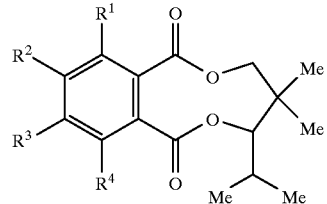

(III)

where $R^1$, $R^2$, $R^3$, and $R^4$ are, independently, hydrogen, a substituted or unsubstituted $C_1$–$C_{10}$ alkyl, aryl, or heteroaryl group, a nitro group, a halo group, a thio group, or an amino group; and any two adjacent substituents of $R^1$, $R^2$, $R^3$, and $R^4$ when taken together with the phenyl ring forms a fused aromatic ring structure.

11. A method of claim 10, wherein $R^1$, $R^2$, $R^3$, and $R^4$ are each a hydrogen.

12. A method of claim 10, wherein said catalyst is butyl stannoic acid.

13. A method of claim 10, wherein said heating step is performed under azeotropic distillation conditions.

* * * * *